(12) United States Patent
Aoude et al.

(10) Patent No.: US 9,545,239 B2
(45) Date of Patent: Jan. 17, 2017

(54) X-RAY DETECTION DEVICE FOR C-ARM TRACKER AND METHOD

(75) Inventors: Ahmed Aoude, Pointe-Claire (CA); Louis-David Parenteau, Verdun (CA); Mélanie Chassé, Deux-Montagnes (CA)

(73) Assignee: ORTHOSOFT INC., Montreal, Quebec (CA)

( * ) Notice: Subject to any disclaimer, the term of this patent is extended or adjusted under 35 U.S.C. 154(b) by 711 days.

(21) Appl. No.: 12/918,020

(22) PCT Filed: Jul. 28, 2009

(86) PCT No.: PCT/CA2009/001061
§ 371 (c)(1),
(2), (4) Date: Aug. 17, 2010

(87) PCT Pub. No.: WO2010/012089
PCT Pub. Date: Feb. 4, 2010

(65) Prior Publication Data
US 2011/0116601 A1 May 19, 2011

Related U.S. Application Data

(60) Provisional application No. 61/083,985, filed on Jul. 28, 2008.

(51) Int. Cl.
*A61B 6/00* (2006.01)
*G01D 18/00* (2006.01)
(Continued)

(52) U.S. Cl.
CPC ............. *A61B 6/584* (2013.01); *A61B 6/4208*
(2013.01); *A61B 6/4225* (2013.01); *A61B 6/4233* (2013.01); *A61B 6/4266* (2013.01); *A61B 6/4441* (2013.01); *A61B 6/56* (2013.01); *A61B 6/563* (2013.01); *A61B 6/58* (2013.01); *A61B 6/582* (2013.01); *A61B 6/583* (2013.01); *A61B 34/20* (2016.02); *A61B 2017/00221* (2013.01); *A61B 2034/2074* (2016.02)

(58) Field of Classification Search
USPC .......... 378/98.8, 207, 196, 197; 250/370.09; 600/407, 425, 426
See application file for complete search history.

(56) References Cited

U.S. PATENT DOCUMENTS

| | | | | |
|---|---|---|---|---|
| 5,444,756 A | * | 8/1995 | Pai ........................ | G01T 1/2018 348/E5.086 |
| 6,118,845 A | * | 9/2000 | Simon et al. .................. | 378/62 |

(Continued)

OTHER PUBLICATIONS

International Search Report, PCT/CA2009/001061, Nov. 6, 2009.

*Primary Examiner* — Allen C. Ho
(74) *Attorney, Agent, or Firm* — Norton Rose Fulbright Canada LLP

(57) ABSTRACT

A detection device for detecting X rays and signaling the detection to a computer-assisted surgery processor system comprises an X ray detector unit having an X ray detector adapted to be positioned within a radiation field. The X ray detector emits a detection signal upon being excited by an X ray of a given intensity. A transmitter outputs the detection signal in radio frequency. A receiver receives the detection signal in radio frequency and forwards the detection signal to a computer-assisted surgery processor system to signal the detection of the X ray. A method is provided as well.

12 Claims, 2 Drawing Sheets

(51) Int. Cl.
*G01T 1/16* (2006.01)
*G01T 1/20* (2006.01)
*G01T 1/24* (2006.01)
*G01T 1/29* (2006.01)
A61B 17/00 (2006.01)

(56) References Cited

U.S. PATENT DOCUMENTS

| | | | |
|---|---|---|---|
| 6,285,902 B1* | 9/2001 | Kienzle et al. | 600/427 |
| 6,379,043 B1* | 4/2002 | Zylka et al. | 378/207 |
| 6,470,207 B1* | 10/2002 | Simon et al. | 378/207 |
| 6,585,412 B2* | 7/2003 | Mitschke | 378/207 |
| 6,696,687 B1* | 2/2004 | Tomisaki et al. | 250/370.09 |
| 6,739,752 B2* | 5/2004 | Sabczynski et al. | 378/207 |
| 6,776,526 B2* | 8/2004 | Zeiss | 378/207 |
| 6,851,855 B2* | 2/2005 | Mitschke et al. | 378/207 |
| 7,065,393 B2* | 6/2006 | Sati et al. | 600/407 |
| 7,382,859 B2* | 6/2008 | Nokita et al. | 378/98.8 |
| 7,542,791 B2* | 6/2009 | Mire et al. | 600/407 |
| 7,622,889 B2* | 11/2009 | Spahn | G03B 42/02 136/293 |
| 7,628,538 B2* | 12/2009 | Dehler | 378/207 |
| 7,922,391 B2* | 4/2011 | Essenreiter et al. | 378/207 |
| 2004/0087852 A1 | 5/2004 | Chen et al. | |
| 2005/0054915 A1 | 3/2005 | Sukovic et al. | |
| 2005/0197569 A1* | 9/2005 | McCombs | A61B 17/154 600/426 |
| 2007/0238984 A1 | 10/2007 | Maschke et al. | |
| 2008/0064952 A1 | 3/2008 | Li et al. | |

* cited by examiner

X-RAY DETECTION DEVICE FOR C-ARM TRACKER AND METHOD

CROSS-REFERENCE TO RELATED APPLICATION

The present application claims U.S. Provisional Patent Application No. 61/083,985, filed on Jul. 28, 2008.

FIELD OF THE APPLICATION

The present application relates to computer-assisted surgery, and more particularly to C-arm imaging and tracking.

BACKGROUND OF THE ART

C-arm units are commonly used in order to obtain X-ray images of bodily parts during surgery. C-arm trackers have been integrated in computer-assisted surgery (CAS), by the addition of a C-arm tracker to a C-arm unit, in order to allow image-based navigation. As the accuracy of the computer-assisted surgery is dependent on the quality of the images, the C-arm tracker is used to relate the X-ray image to the tracking of the bodily part.

The relation between the X-ray image and the tracking of the bodily part is obtained by tracking the C-arm tracker to provide a scale relation between the image and the bodily part. Because of accuracy requirements for CAS surgery, the positional relation between the C-arm tracker and the tracked bodily part must be recorded at the time that the image is taken, for instance to avoid errors due to movement between the patient and the C-arm tracker, from the moment the X-ray is taken and to the moment the X-ray image file is converted to navigation data.

Accordingly, diodes are commonly used to detect X-rays. More specifically, diodes are provided on the C-arm tracker and are wired to the CAS processor system so as to detect and signal the detection of X-rays. With the signaling of the X-ray, the CAS processor system simultaneously records the positional relation between the C-arm tracker and the patient. The positional relation is then used in the conversion of the X-ray image to navigation data, for instance to adjust the orientation of the image.

SUMMARY OF THE APPLICATION

It is therefore an aim of the present disclosure to provide a novel X-ray detection device for C-arm tracker, and a method of signaling detection.

It is a further aim of the present disclosure to provide a novel method for the calibration of a C-arm tracker.

Therefore, in accordance with a first embodiment, there is provided a detection device for detecting X-rays and signaling the detection to a computer-assisted surgery processor system, comprising: an X-ray detector unit having an X-ray detector adapted to be positioned within a radiation field, the X-ray detector emitting a detection signal upon being excited by an X-ray of a given intensity; a transmitter for outputting the detection signal in radio frequency; and a receiver for receiving the detection signal in radio frequency and for forwarding the detection signal to a computer-assisted surgery processor system to signal the detection of the X-ray.

Further in accordance with the first embodiment, the detection device is adapted to detect X-rays from a C-arm, and the X-ray detector unit further comprises a memory for storing a definition file of a C-arm tracker used with the C-arm, the transmitter and the receiver wirelessly transmitting in radio frequency the definition file to the computer-assisted surgery processor system.

Still further in accordance with the first embodiment, the detection device is adapted to detect X-rays from a C-arm, and the X-ray detector is mounted directly to a C-arm tracker.

Still further in accordance with the first embodiment, the X-ray detector comprises a plurality of scintillator diodes mounted to a rim of the C-arm tracker.

Still further in accordance with the first embodiment, X-ray detector comprises at least one scintillator diode emitting the detection signal when excited by an X-ray, the detection signal being proportional to an intensity of the X-ray.

Still further in accordance with the first embodiment, the X-ray detector unit has a processor measuring an intensity of the detection signal, the transmitter outputting the detection signal if the measured intensity is above a threshold intensity.

Still further in accordance with the first embodiment, the X-ray detector unit has a processor measuring an intensity of the X-ray, the processor emitting the detection signal if the measured intensity is above a threshold intensity.

Still further in accordance with the first embodiment, the transmitter outputs the detection signal is in synchronization with a falling edge of a radiation wave of the X-ray detected by the X-ray detector.

In accordance with a second embodiment embodiment, there is provided a method for signaling a detection of an X-ray to a computer-assisted surgery processor system, comprising: activating an X-ray detection in a radiation field; producing a detection signal upon detecting an X-ray of a given intensity in the radiation field; and transmitting the detection signal to a computer-assisted surgery processor system using radio frequency.

Further in accordance with the second embodiment, the method is used to detect X-rays from a C-arm, the method further comprising storing a definition file of a C-arm tracker, and transmitting the definition file to the computer-assisted surgery system using radio frequency.

Still further in accordance with the second embodiment, producing a detection signal comprises determining whether the intensity of the X-ray is above an intensity threshold, and transmitting the detection signal comprises transmitting the detection signal if the intensity of the X-ray is above the intensity threshold.

Still further in accordance with the second embodiment, the method is used to detect X-rays from a C-arm, and further wherein activating the X-ray detection comprises mounting an X-ray detector to a C-arm tracker.

Still further in accordance with the second embodiment, transmitting the detection signal comprises synchronizing the transmission with a falling edge of a radiation wave of the detected X-ray.

DESCRIPTION OF PREFERRED EMBODIMENTS

Figure 1:
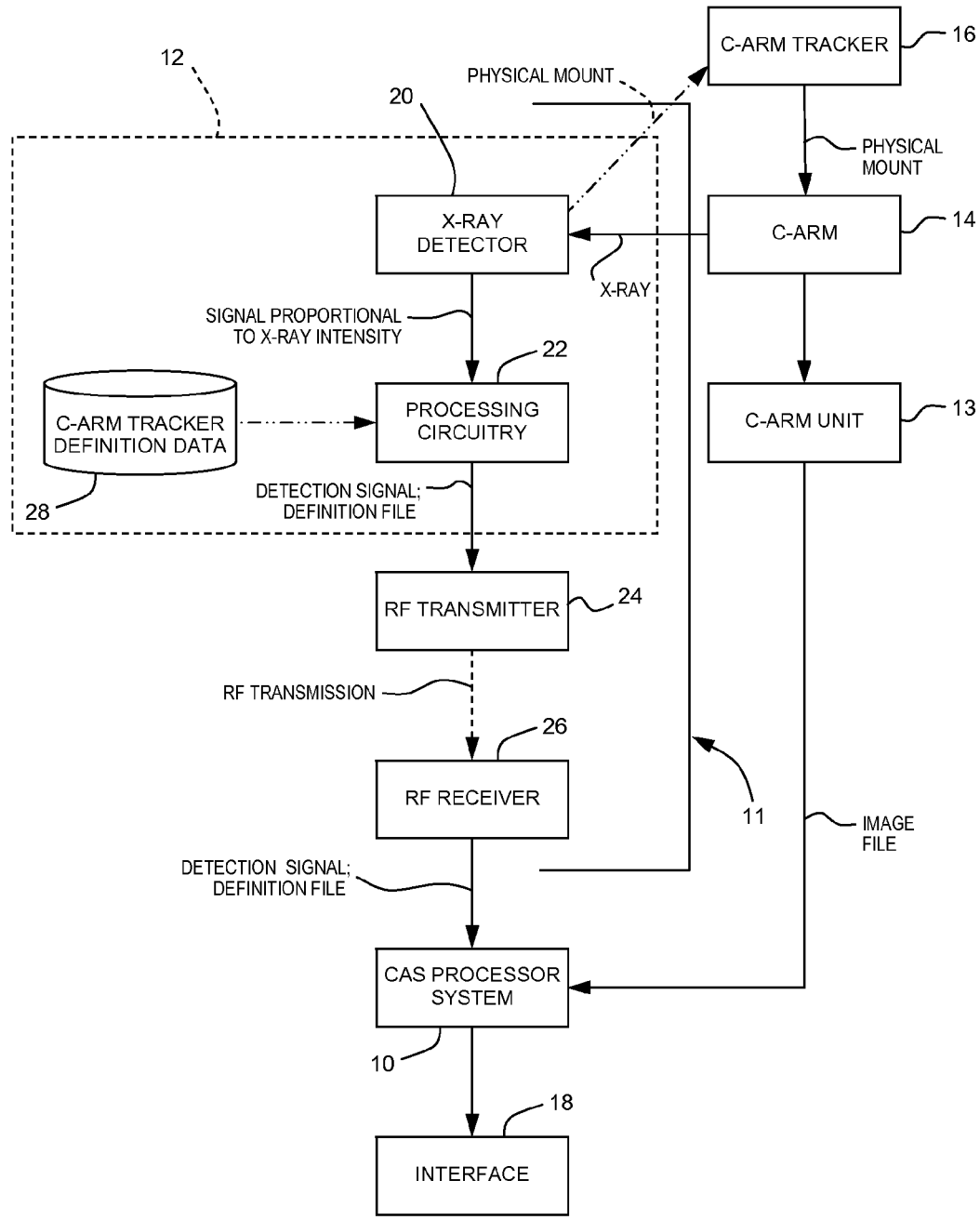
FIG. 1 is a block diagram of a computer-assisted surgery processor system used with a C-arm and with an X-ray detection device in accordance with a preferred embodiment of the present disclosure.

Referring to FIG. 1, an X-ray detection device as used with a computer-assisted surgery (CAS) processor system 10 is generally illustrated at 11. The X-ray detection device 11 is used in combination with the CAS processor system 10 to signal the acquisition of an image from a C-arm unit 13. The X-ray detection device 11 has an X-ray detection unit 12 and is used during computer-assisted surgical procedures in which image-based navigation is performed, such as spine surgery (pedical screw placement) and some types of traumatology surgery or any type of surgery using fluoroscopy technology for image-based navigation.

As known in the art, the C-arm unit 13 (i.e. processing unit) is connected to a C-arm 14 (encompassing an X-ray source and an image intensifier) obtaining X-ray images of a bodily part, such as a spine. A C-arm tracker 16 is physically mounted to the C-arm 14 for the subsequent image-based navigation during the surgical procedure. As known in the art, the C-arm tracker 16 provides a plate with a bead pattern for the calibration of the image, in order to ensure its accurate reproduction (e.g., dewarping) by the CAS processor system 10 in view of the navigation. The CAS processor system 10 tracks a position and orientation of the C-arm tracker 16 so as to relate the images obtained from the C-arm 14 to the tracking of the bodily part. As a known solution for the tracking, both the C-arm tracker 16 and the bodily part are tracked using passive optical tracking (e.g., a Northern Digital™ system). Alternatives to passive optical tracking are considered and used as well (e.g., active sensors, such as infrared LEDs, magnetic emitters, and any other suitable tracking system, etc).

The image-based navigation data is output on an interface 18. For instance, visual representations of tools are provided in real-time with respect to X-ray images of a portion of a spine.

The X-ray detection device 11 is a self-powered (e.g., battery operated) device that detects X-rays and signals the X-ray detection to a CAS processor system 10 with an excitation signal separate from the imaging (e.g., detection is separate from imaging). The X-ray detection unit 12 has an X-ray detector 20 to detect the X-rays. Accordingly, the X-ray detector 20 is positioned in the field of radiation of the C-arm 14. In an embodiment, the X-ray detector 20 is physically mounted to the C-arm tracker 16, so as to avoid any obstruction of the detector 20 in the field of radiation, for instance by the presence of metallic tools or the like.

In an embodiment, the X-ray detector 20 has scintillator diodes separate from imaging equipment that are excited by the X-ray. Scintillator diodes generate a signal proportional to an X-ray intensity. Other types of diodes excited by the detection of X-rays are also considered. In another embodiment, one or more scintillator diodes are distributed on the circular rim of the C-arm tracker 16, to ensure that at least one of the scintillator diodes detects the X-ray emission.

According to the type of X-ray detector 20 used, the signal from the X-ray detector 20 may require to be amplified. The X-ray detection unit 12 with the scintillator diodes has a processing circuit 22. The processing circuit 22 also filters out detected light of insufficient intensity. For instance, residual radiation and backscatter should not be detected by the X-ray detector 20, whereby the processing circuit 22 has a threshold value for the radiation intensity. If the intensity of the amplified detected radiation is above the threshold value, the processing circuit 22 produces a detection signal that is transmitted to the CAS processor system 10. Filtering out of detected light of insufficient intensity may be performed by the CAS processor system 10.

The X-ray detection device 11 also has a radio-frequency (RF) transmitter 24 that is connected to the processing circuit 22 to produce an RF transmission indicative of the detection signal. In the embodiment in which the X-ray detector 20 is mounted to the C-arm tracker 16, the processing circuit 22 and the RF transmitter 24 are also mounted to the C-arm tracker 16.

The X-ray detection device 11 also has an RF receiver 26 is connected to the CAS processor system 10, and is configured to receive the RF transmission from the RF transmitter 24, for wireless transmission of the detection signal. The RF transmitter 24 and the RF receiver 26 may be self-powered and configured to send appropriate signals to the CAS processor system 10.

By using RF technology for the transmission of the detection signal, there is no need for a line of sight between the RF receiver 26 of the CAS processor system 10 and the X-ray detection device 11. Moreover, by the use of self-powered wireless transmission, there are no wires relating the X-ray detection device 11 to the CAS processor system 10, whether it be for the transmission of data or to supply power to the device 11. Bluetooth, wi-fi, Zigbee standards are amongst the various standards considered for the RF transmission.

According to an embodiment, the X-ray detector 20 is included in the C-arm tracker 16, and stores C-arm calibration data 28. The C-arm calibration data 28 is used by the CAS processor system 10 to identify the C-arm tracker 16. As each C-arm tracker 16 has individual specifications (e.g., orientation of plate and bead pattern, types of trackers used, position and orientation of trackers on the C-arm tracker 16), the CAS processor system 10 must calibrate the C-arm tracker 16, for instance by receiving a definition file for the C-arm tracker 16. The definition file may simply consist of an identification of the C-arm tracker 16 for the CAS processor system 10 to obtain a calibration data from another source, or may comprise additional information (e.g., orientation data). In an embodiment, the definition file comprises relational data related to the bead pattern of the plate of the C-arm tracker 16.

Figure 2:
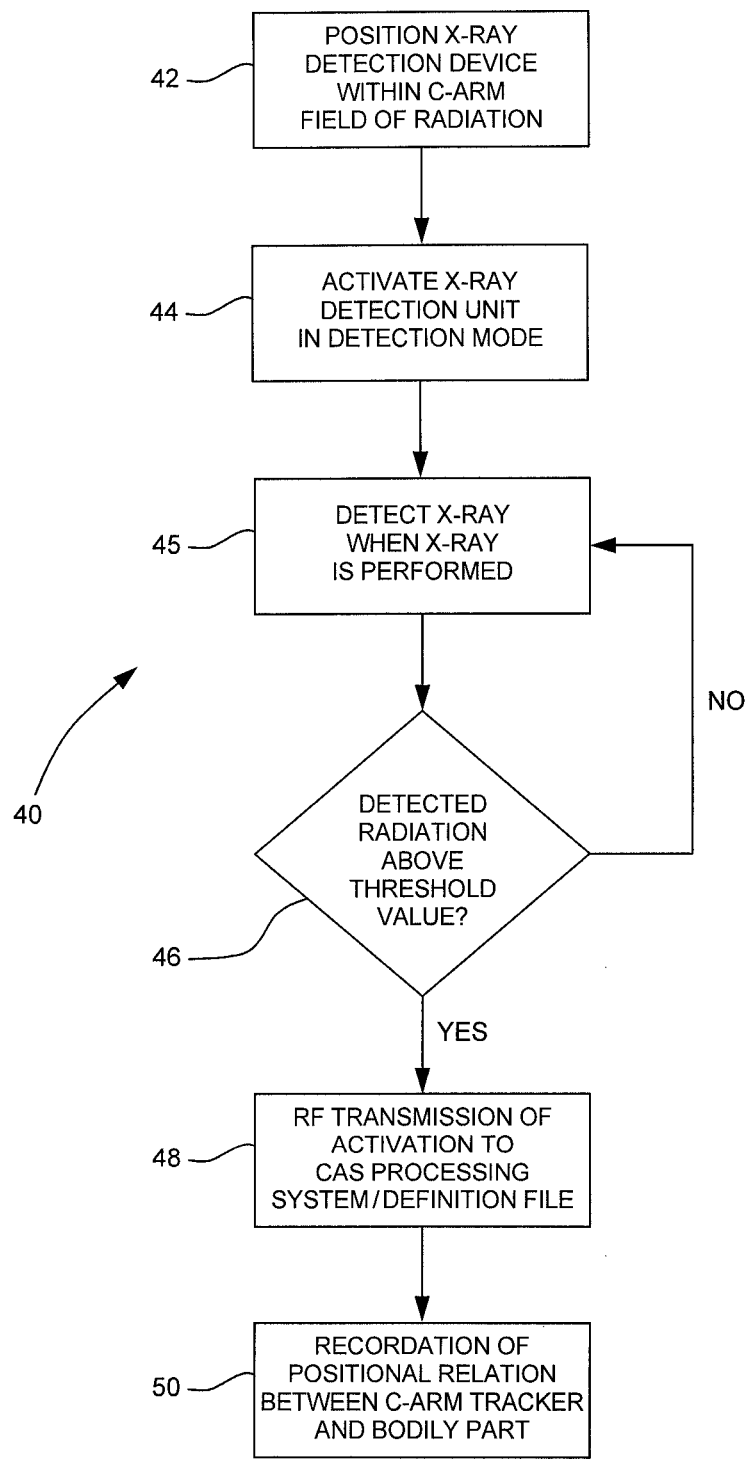
FIG. 2 is a flow chart illustrating a method for signaling an X-ray to a CAS processor system in accordance with another preferred embodiment of the present disclosure.

Referring to FIG. 2, now that the X-ray detection device 11 has been described, a method 40 of using the X-ray detection device 11 is described.

According to Step 42, the X-ray detector 20 is positioned within the field of radiation of the C-arm 14, whereby emission of radiation by the C-arm 14 is detected by the X-ray detector 20.

According to Step 44, the X-ray detection unit 12 is activated to a detection mode.

According to Step 45, the X-ray is detected by the detector 20 when the X-ray is performed.

At Decision 46, upon detecting radiation and treating the resulting radiation signal, the X-ray detection unit 12 compares the intensity of the radiation to a threshold value. If the X-ray detection signal is below the threshold value, the X-ray detection unit 12 is idle.

According to Step 48, if the intensity is above the threshold value, an X-ray detection signal is transmitted to the CAS processor system 10 using RF transmission to indicate that an X-ray is detected. In an embodiment, the transmission of the X-ray detection signal by the RF transmitter 24 is synchronized with the falling edge of the radiation wave detected by the X-ray detector 20. The definition file is optionally transmitted to the CAS processor system 10 using RF transmission, to calibrate the C-arm tracker 16 with the CAS processor system 10. The definition file may be transmitted at any other time prior to Step 48.

According to Step 50, the positional relation between the C-arm tracker 16 and the tracked bodily part is recorded by the CAS processor system 10 upon reception of the RF transmission from the X-ray detection device 11. Therefore, the image file, the positional relation and optionally the definition file are used to convert the X-ray image to navigation data.

The invention claimed is:

1. An assembly of a computer-assisted surgery processor system and a detection device for detecting X-rays and signaling the detection to the computer-assisted surgery processor system, comprising:
   the detection device comprising:
      an X-ray detector unit having an X-ray detector separate from X-ray imaging equipment and adapted to be positioned within a radiation field, the X-ray detector emitting a detection signal upon being excited by an X-ray beam of a given intensity;
      a transmitter for outputting the detection signal in radio frequency; and
      a receiver for receiving the detection signal in radio frequency and for forwarding the detection signal to the computer-assisted surgery processor system to signal the detection of the X-ray beam; and
   the computer-assisted surgery processor system for recording a positional relation between a patient and imaging equipment as a response to the detection signal.

2. The assembly according to claim 1, wherein the detection device is adapted to detect X-rays from a C-arm, and the X-ray detector unit further comprises a memory for storing a definition file of a C-arm tracker used with the C-arm, the transmitter and the receiver wirelessly transmitting in radio frequency the definition file to the computer-assisted surgery processor system.

3. The assembly according to claim 1, wherein the detection device is adapted to detect X-rays from a C-arm, the imaging equipment is a C-arm tracker and the X-ray detector is mounted directly to the C-arm tracker.

4. The assembly according to claim 1, the X-ray detector comprises at least one scintillator diode emitting the detection signal when excited by an X-ray, the detection signal being proportional to an intensity of the X-ray.

5. The assembly according to claim 1, wherein the X-ray detector unit has a processor measuring an intensity of the detection signal, the transmitter outputting the detection signal if the measured intensity is above a threshold intensity.

6. The assembly according to claim 1, wherein the X-ray detector unit has a processor measuring an intensity of the X-ray beam, the processor emitting the detection signal if the measured intensity is above a threshold intensity.

7. The assembly according to claim 1, wherein the transmitter outputs the detection signal is in synchronization with a falling edge of a radiation wave of the X-ray beam detected by the X-ray detector.

8. A method for signaling a detection of an X-ray to a computer-assisted surgery processor system, comprising:
   activating an X-ray detection in a radiation field separate from an imaging equipment;
   producing a detection signal upon detecting an X-ray beam of a given intensity in the radiation field; and
   transmitting the detection signal to a computer-assisted surgery processor system using radio frequency; and
   recording a positional relation between a patient and the imaging equipment with the computer-assisted surgery processor system as a response to receiving the transmitted detection signal.

9. The method according to claim 8, further comprising:
   using the activating, the producing and the transmitting to detect X-rays from a C-arm;
   storing a definition file of a C-arm tracker; and
   transmitting the definition file to the computer-assisted surgery processor system using radio frequency.

10. The method according to claim 8, wherein producing a detection signal comprises determining whether the intensity of the X-ray beam is above an intensity threshold, and transmitting the detection signal comprises transmitting the detection signal if the intensity of the X-ray beam is above the intensity threshold.

11. The method according to claim 8, further comprising:
   using the activating, the producing and the transmitting to detect X-rays from a C-arm with the imaging equipment being a C-arm tracker; and
   further wherein activating an X-ray detection comprises mounting an X-ray detector to the C-arm tracker.

12. The method according to claim 8, wherein transmitting the detection signal comprises synchronizing the transmission with a falling edge of a radiation wave of the detected X-rays.

* * * * *